US 8,076,275 B2
Dec. 13, 2011

(12) United States Patent
Ruhe, Jr. et al.

(54) REDUCED COLOR MOLYBDENUM-CONTAINING COMPOSITION AND A METHOD OF MAKING SAME

(75) Inventors: William R. Ruhe, Jr., Benicia, CA (US); Anatoli Onopchenko, Concord, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 1210 days.

This patent is subject to a terminal disclaimer.

(21) Appl. No.: 11/082,351

(22) Filed: Mar. 17, 2005

(65) Prior Publication Data

US 2005/0209111 A1  Sep. 22, 2005

Related U.S. Application Data

(63) Continuation of application No. 10/159,446, filed on May 31, 2002, now Pat. No. 6,962,896.

(51) Int. Cl.
*C10M 159/18* (2006.01)

(52) U.S. Cl. .......................... 508/230; 508/362; 508/367

(58) Field of Classification Search .................. 508/230, 508/362, 367
See application file for complete search history.

(56) References Cited

U.S. PATENT DOCUMENTS

| 4,239,633 A | 12/1980 | Gutierrez et al. |
| 4,263,152 A | 4/1981 | King et al. |
| 4,272,387 A | 6/1981 | King et al. |
| 4,285,822 A * | 8/1981 | deVries et al. .............. 508/230 |
| 4,369,119 A | 1/1983 | deVries et al. |
| 4,370,246 A | 1/1983 | deVries et al. |
| 4,395,343 A | 7/1983 | deVries et al. |
| 5,650,381 A | 7/1997 | Gatto et al. |
| 5,840,672 A | 11/1998 | Gatto |
| 5,895,779 A | 4/1999 | Boffa |
| 6,174,842 B1 | 1/2001 | Gatto et al. |
| 6,962,896 B2 * | 11/2005 | Ruhe et al. .................. 508/230 |

FOREIGN PATENT DOCUMENTS

| CA | 1 125 735 | 6/1982 |
| EP | 0 205 165 | 1/1991 |
| EP | 1 136 496 B1 | 9/2001 |
| GB | 2 037 317 A | 7/1980 |
| GB | 2 097 422 A | 11/1982 |
| WO | WO 94/06897 | 3/1994 |
| WO | WO 01/46352 A1 | 6/2001 |

* cited by examiner

*Primary Examiner* — Jim Goloboy

(74) *Attorney, Agent, or Firm* — Josetta I. Jones; Michael Carmen

(57) ABSTRACT

Antioxidant additives for lubricating oils are prepared by reacting an acidic molybdenum compound or salt thereof and a basic nitrogen compound where the temperature of the process does not exceed 120° C., resulting in a product color that is light in intensity.

8 Claims, No Drawings

REDUCED COLOR MOLYBDENUM-CONTAINING COMPOSITION AND A METHOD OF MAKING SAME

This application is a continuation of co-pending application U.S. Ser. No. 10/159,446 and, under 35 U.S.C. 120, claims the benefit of the May 31, 2002 filing date of the co-pending application.

BACKGROUND OF INVENTION

1. Field of the Invention

This invention relates to the manufacture and composition of lubricating oil additives, particularly to molybdenum-containing compositions.

2. Background

Compositions of molybdic acid and oil soluble basic nitrogen containing compounds have been used as lubricating oil additives to control oxidation and wear of engine components. Since their discovery, such complexes have been widely used as engine lubricating oil additives in automotive and diesel crankcase oils and as an additive in some two-cycle oils to prevent valve sticking. Generally, these compounds are added to a detergent package that is added to engine lubricating oils.

Complexes of molybdic acid and oil soluble basic nitrogen containing compounds are normally made with an organic solvent during a molybdenum-containing composition complexation step. The complexation step can be followed by a sulfurization step as disclosed in King et al., U.S. Pat. No. 4,263,152, which is herein incorporated by reference. Related King et al., U.S. Pat. No. 4,272,387, is also incorporated by reference.

After sulfurization, these compositions are extremely dark in color. These compositions are measured at about 5 triple dilute (DDD) using an ASTM D1500 or ASTM D6045 colorimetric test. Since low color lubricating oils are highly desired in the marketplace, these dark compositions can only be used in limited doses because of the impact they have on the finished oil color.

Other related references are: Gatto et al., U.S. Pat. No. 5,650,381, disclose lubricating compositions that contain (a) an active sulfur-free soluble molybdenum compound; and (b) an oil soluble secondary diarylamine; Gatto, U.S. Pat. No. 5,840,672, discloses an antioxidant system for lubricating oil compositions that includes (a) a secondary diarylamine; (b) a sulfurized olefin or sulfurized hindered phenol; and (c) an oil soluble unsulfurized or sulfur-containing molybdenum compound; and Gatto et al., U.S. Pat. No. 6,174,842, disclose lubricants containing (a) molybdenum compounds substantially free of reactive sulfur; (b) phenates; and (c) diarylamines.

SUMMARY OF THE INVENTION

The present invention provides a novel product for a low color intensity, oil-soluble molybdenum-containing composition prepared by a process comprising: (a) reacting an acidic molybdenum compound or salt thereof and a basic nitrogen compound selected from the group consisting of succinimides, carboxylic acid amides, hydrocarbyl monoamines, hydrocarbon polyamines, Mannich bases, phosphonoamides, thiophosphonamides, phosphoramides, dispersant viscosity index improvers, and mixtures thereof, to form a molybdenum complex wherein the temperature of the reaction is maintained at or below about 120° C.; and (b) sulfurizing the resulting product of step (a) at a temperature at or below 120° C. and wherein the sulfur to molybdenum atomic ratio is less than 0.1:1 for a period of time sufficient to provide an oil-soluble molybdenum containing composition having an absorbance intensity of less than 0.7 at a wavelength of 350 nanometers as measured in a one centimeter path-length quartz cell in a UV-Visible spectrophotometer by diluting the molybdenum containing composition with isooctane to a constant molybdenum concentration of 0.00025 grams of molybdenum per gram of the diluted molybdenum containing composition.

The present invention also provides a product prepared by a process comprising: (a) reacting an acidic molybdenum compound or salt thereof and a basic nitrogen compound selected from the group consisting of succinimides, carboxylic acid amides, hydrocarbyl monoamines, hydrocarbon polyamines, Mannich bases, phosphonoamides, thiophosphonamides, phosphoramides, dispersant viscosity index improvers, and mixtures thereof, to form a molybdenum complex wherein the temperature of the reaction is maintained at or below about 120° C.; (b) stripping the product of (a) at a temperature at or below about 120° C.; and (c) sulfurizing the resulting product at a temperature at or below 120° C. and wherein the sulfur to molybdenum atomic ratio is about 0.1:1 or less for a period of time sufficient to provide an oil-soluble molybdenum containing composition having an absorbance intensity of less than 0.7 at a wavelength of 350 nanometers as measured in a one centimeter path-length quartz cell in a UV-Visible spectrophotometer by diluting the molybdenum containing composition with isooctane to a constant molybdenum concentration of 0.00025 grams of molybdenum per gram of the diluted molybdenum containing composition.

Moreover, the present invention also provides a lubricating oil composition and a lubricating oil concentrate containing the product prepared by the process of the invention.

A new method has now been discovered in which a low color intensity molybdenum-containing composition may be manufactured with or without an organic solvent, in the presence of an aqueous promoter, and at a process temperature that does not exceed 120° C. This new process also includes an optional sulfurization step that is carried out at temperatures less than 120° C. The product made by this process is light in color, exhibits good frictional properties, has good oxidation inhibition, and good anti-wear performance.

DETAILED DESCRIPTION OF THE INVENTION

The sulfurized or unsulfurized molybdenum-containing composition of the present invention may be generally characterized as containing a molybdenum or molybdenum/sulfur complex of a basic nitrogen compound. The exact molecular formula of the molybdenum compositions of this invention is not known with certainty; however, such compositions are believed to contain compounds in which molybdenum, whose valences are satisfied with atoms of oxygen and/or sulfur, is either complexed by, or the salt of, one or more nitrogen atoms of the basic nitrogen containing compound used in the preparation of these compositions.

The molybdenum compounds used to prepare the molybdenum, or molybdenum/sulfur compositions of this invention are acidic molybdenum compounds or salts of acidic molybdenum compounds. By acidic is meant that the molybdenum compounds will react with a basic nitrogen compound in which the basicity of the basic nitrogen compound can be determined by ASTM test D664 or the D2896 titration procedure. Typically, these molybdenum compounds are hexavalent and are represented by the following compositions:

molybdic oxide, molybdic acid, ammonium molybdate, sodium molybdate, potassium molybdates and other alkaline metal molybdates and other molybdenum salts such as hydrogen salts, e.g., hydrogen sodium molybdate, $MoOCl_4$, $MoO_2Br_2$, $Mo_2O_3Cl_6$, molybdenum trioxide or similar acidic molybdenum compounds. Preferred acidic molybdenum compounds are molybdic oxide, molybdic acid, ammonium molybdate, and alkali metal molybdates. Particularly preferred is molybdic oxide.

The basic nitrogen compound used to prepare the molybdenum/sulfur compositions must contain basic nitrogen as measured by ASTM D664 test or ASTM D2896. It is preferably oil-soluble. The basic nitrogen compound is selected from the group consisting of succinimides, carboxylic acid amides, hydrocarbyl monoamines, hydrocarbon polyamines, Mannich bases, phosphoramides, thiophosphoramides, phosphonamides, dispersant viscosity index improvers, and mixtures thereof. These basic nitrogen-containing compounds are described below (keeping in mind the reservation that each must have at least one basic nitrogen). Any of the nitrogen-containing compositions may be post-treated with, e.g., boron, using procedures well known in the art so long as the compositions continue to contain basic nitrogen. These post-treatments are particularly applicable to succinimides and Mannich base compositions.

The succinimides and polysuccinimides that can be used to prepare the molybdenum/sulfur compositions described herein are disclosed in numerous references and are well known in the art. Certain fundamental types of succinimides and the related materials encompassed by the term of art "succinimide" are taught in U.S. Pat. Nos. 3,219,666; 3,172,892; and 3,272,746, the disclosures of which are hereby incorporated by reference. The term "succinimide" is understood in the art to include many of the amide, imide, and amidine species which may also be formed. The predominant product, however, is a succinimide and this term has been generally accepted as meaning the product of a reaction of an alkenyl substituted succinic acid or anhydride with a nitrogen-containing compound. Preferred succinimides, because of their commercial availability, are those succinimides prepared from a hydrocarbyl succinic anhydride, wherein the hydrocarbyl group contains from about 24 to about 350 carbon atoms, and an ethylene amine, said ethylene amines being especially characterized by ethylene diamine, diethylene triamine, triethylene tetramine, tetraethylene pentamine, and higher molecular weight polyethylene amines. Particularly preferred are those succinimides prepared from polyisobutenyl succinic anhydride of 70 to 128 carbon atoms and tetraethylene pentamine or higher molecular weight polyethylene amines or mixtures of polyethylene amines such that the average molecular weight of the mixture is about 205 Daltons thereof.

Also included within the term "succinimide" are the cooligomers of a hydrocarbyl succinic acid or anhydride and a polysecondary amine containing at least one tertiary amino nitrogen in addition to two or more secondary amino groups. Ordinarily, this composition has between 1,500 and 50,000 average molecular weight. A typical compound would be that prepared by reacting polyisobutenyl succinic anhydride and ethylene dipiperazine.

Carboxylic acid amide compounds are also suitable starting materials for preparing the molybdenum or molybdenum/sulfur compositions of this invention. Typical of such compounds are those disclosed in U.S. Pat. No. 3,405,064, the disclosure of which is hereby incorporated by reference. These compounds are ordinarily prepared by reacting a carboxylic acid or anhydride or ester thereof, having at least 12 to about 350 aliphatic carbon atoms in the principal aliphatic chain and, if desired, having sufficient pendant aliphatic groups to render the molecule oil soluble with an amine or a hydrocarbyl polyamine, such as an ethylene amine, to give a mono or polycarboxylic acid amide. Preferred are those amides prepared from (1) a carboxylic acid of the formula $R^2COOH$, where $R^2$ is $C_{12-20}$ alkyl or a mixture of this acid with a polyisobutenyl carboxylic acid in which the polyisobutenyl group contains from 72 to 128 carbon atoms and (2) an ethylene amine, especially triethylene tetramine or tetraethylene pentamine or mixtures thereof.

Another class of compounds which are useful in this invention are hydrocarbyl monoamines and hydrocarbyl polyamines, preferably of the type disclosed in U.S. Pat. No. 3,574,576, the disclosure of which is hereby incorporated by reference. The hydrocarbyl group, which is preferably alkyl, or olefinic having one or two sites of unsaturation, usually contains from 9 to 350, preferably from 20 to 200 carbon atoms. Particularly preferred hydrocarbyl polyamines are those which are derived, e.g., by reacting polyisobutenyl chloride and a polyalkylene polyamine, such as an ethylene amine, e.g., ethylene diamine, diethylene triamine, tetraethylene pentamine, 2-aminoethylpiperazine, 1,3-propylene diamine, 1,2-propylenediamine, and the like.

Another class of compounds useful for supplying basic nitrogen are the Mannich base compounds. These compounds are prepared from a phenol or $C_{9-200}$ alkylphenol, an aldehyde, such as formaldehyde or formaldehyde precursor such as paraformaldehyde, and an amine compound. The amine may be a mono or polyamine and typical compounds are prepared from an alkylamine, such as methylamine or an ethylene amine, such as, diethylene triamine, or tetraethylene pentamine, and the like. The phenolic material may be sulfurized and preferably is dodecylphenol or a $C_{80-100}$ alkylphenol. Typical Mannich bases which can be used in this invention are disclosed in U.S. Pat. Nos. 4,157,309 and 3,649,229; 3,368,972; and 3,539,663, the disclosures of which are hereby incorporated by reference. The last referenced patent discloses Mannich bases prepared by reacting an alkylphenol having at least 50 carbon atoms, preferably 50 to 200 carbon atoms with formaldehyde and an alkylene polyamine $HN(ANH)_nH$ where A is a saturated divalent alkyl hydrocarbon of 2 to 6 carbon atoms and n is 1 to 10 and where the condensation product of said alkylene polyamine may be further reacted with urea or thiourea. The utility of these Mannich bases as starting materials for preparing lubricating oil additives can often be significantly improved by treating the Mannich base using conventional techniques to introduce boron into the compound.

Another class of compounds useful for preparing the molybdenum or molybdenum/sulfur compositions of this invention are the phosphoramides and phosphonamides such as those disclosed in U.S. Pat. Nos. 3,909,430 and 3,968,157, the disclosures of which are hereby incorporated by reference. These compounds may be prepared by forming a phosphorus compound having at least one P—N bond. They can be prepared, for example, by reacting phosphorus oxychloride with a hydrocarbyl diol in the presence of a monoamine or by reacting phosphorus oxychloride with a difunctional secondary amine and a mono-functional amine. Thiophosphoramides can be prepared by reacting an unsaturated hydrocarbon compound containing from 2 to 450 or more carbon atoms, such as polyethylene, polyisobutylene, polypropylene, ethylene, 1-hexene, 1,3-hexadiene, isobutylene, 4-methyl-1-pentene, and the like, with phosphorus pentasulfide and a nitrogen-containing compound as defined above, particularly an alkylamine, alkyldiamine, alkylpolyamine, or an alkyleneamine, such as ethylene diamine, diethylenetriamine, triethylenetetramine, tetraethylenepentamine, and the like.

Another class of nitrogen-containing compounds useful in preparing the molybdenum or molybdenum/sulfur compositions of this invention includes the so-called dispersant viscosity index improvers (VI improvers). These VI improvers are commonly prepared by functionalizing a hydrocarbon polymer, especially a polymer derived from ethylene and/or propylene, optionally containing additional units derived from one or more co-monomers such as alicyclic or aliphatic olefins or diolefins. The functionalization may be carried out by a variety of processes which introduce a reactive site or sites which usually has at least one oxygen atom on the polymer. The polymer is then contacted with a nitrogen-containing source to introduce nitrogen-containing functional groups on the polymer backbone. Commonly used nitrogen sources include any basic nitrogen compound especially those nitrogen-containing compounds and compositions described herein. Preferred nitrogen sources are alkylene amines, such as ethylene amines, alkyl amines, and Mannich bases.

Preferred basic nitrogen compounds for use in this invention are succinimides, carboxylic acid amides, and Mannich bases. The preferred succinimide is prepared from a polyalkylene amine or mixtures thereof reacted with a polyisobutenyl succinic anhydride derived from the reaction of polyisobutylene with maleic anhydride as described in Harrison et al., U.S. Pat. No. 6,156,850.

Representative sulfur sources for preparing the molybdenum or molybdenum/sulfur compositions of this invention are sulfur, hydrogen sulfide, sulfur monochloride, sulfur dichloride, phosphorus pentasulfide, $R_2S_x$ where R is hydrocarbyl, preferably $C_{1-40}$ alkyl, and x is at least 2, inorganic sulfides and polysulfides such as $(NH_4)_2S_x$, where x is at least 1, thioacetamide, thiourea, and mercaptans of the formula RSH where R is as defined above. Also useful as sulfurizing agents are traditional sulfur-containing antioxidants such as wax sulfides and polysulfides, sulfurized olefins, sulfurized carboxylic and esters and sulfurized ester-olefins, and sulfurized alkylphenols and the metal salts thereof.

The sulfurized fatty acid esters are prepared by reacting sulfur, sulfur monochloride, and/or sulfur dichloride with an unsaturated fatty ester under elevated temperatures. Typical esters include $C_1$-$C_{20}$ alkyl esters of $C_8$-$C_{24}$ unsaturated fatty acids, such as palmitoleic, oleic, ricinoleic, petroselinic, vaccenic, linoleic, linolenic, oleostearic, licanic, paranaric, tariric, gadoleic, arachidonic, cetoleic, etc. Particularly good results have been obtained with mixed unsaturated fatty acid esters, such as are obtained from animal fats and vegetable oils, such as tall oil, linseed oil, olive oil, castor oil, peanut oil, rape oil, fish oil, sperm oil, and so forth.

Exemplary fatty esters include lauryl tallate, methyl oleate, ethyl oleate, lauryl oleate, cetyl oleate, cetyl linoleate, lauryl ricinoleate, oleyl linoleate, oleyl stearate, and alkyl glycerides.

Cross-sulfurized ester olefins, such as a sulfurized mixture of $C_{10}$-$C_{25}$ olefins with fatty acid esters of $C_{10}$-$C_{25}$ fatty acids and $C_1$-$C_{25}$ alkyl or alkenyl alcohols, wherein the fatty acid and/or the alcohol is unsaturated may also be used.

Sulfurized olefins are prepared by the reaction of the $C_3$-$C_6$ olefin or a low-molecular-weight polyolefin derived therefrom with a sulfur-containing compound such as sulfur, sulfur monochloride, and/or sulfur dichloride.

Also useful are the aromatic and alkyl sulfides, such as dibenzyl sulfide, dixylyl sulfide, dicetyl sulfide, diparaffin wax sulfide and polysulfide, cracked wax-olefin sulfides and so forth. They can be prepared by treating the starting material, e.g., olefinically unsaturated compounds, with sulfur, sulfur monochloride, and sulfur dichloride. Particularly preferred are the paraffin wax thiomers described in U.S. Pat. No. 2,346,156.

Sulfurized alkyl phenols and the metal salts thereof include compounds such as sulfurized dodecylphenol and the calcium salts thereof. The alkyl group ordinarily contains from 9 to 300 carbon atoms. The metal salt may be preferably, a Group I or Group II salt, especially sodium, calcium, magnesium, or barium.

Preferred sulfur sources are sulfur, hydrogen sulfide, phosphorus pentasulfide, $R_2S_x$ where R is hydrocarbyl, preferably $C_1$-$C_{10}$ alkyl, and x is at least 3, mercaptans wherein R is $C_1$-$C_{10}$ alkyl, inorganic sulfides and polysulfides, thioacetamide, and thiourea. Most preferred sulfur sources are sulfur, hydrogen sulfide, phosphorus pentasulfide, and inorganic sulfides and polysulfides.

The polar promoter used in the preparation of the molybdenum or molybdenum/sulfur compositions of this invention is one which facilitates the interaction between the molybdenum compound and the basic nitrogen compound. A wide variety of such promoters are well known to those skilled in the art. Typical promoters are 1,3-propanediol, 1,4-butanediol, diethylene glycol, butyl cellosolve, propylene glycol, 1,4-butyleneglycol, methyl carbitol, ethanolamine, diethanolamine, N-methyl-diethanol-amine, dimethyl formamide, N-methyl acetamide, dimethyl acetamide, methanol, ethylene glycol, dimethyl sulfoxide, hexamethyl phosphoramide, tetrahydrofuran and water. Preferred are water and ethylene glycol. Particularly preferred is water.

While ordinarily the polar promoter is separately added to the reaction mixture, it may also be present, particularly in the case of water, as a component of non-anhydrous starting materials or as waters of hydration in the acidic molybdenum compound, such as $(NH_4)_6Mo_7O_{24}.4H_2O$. Water may also be added as ammonium hydroxide.

A method for preparing the molybdenum or molybdenum/sulfur compositions of this invention involves preparing a mixture of the molybdenum compound and a polar promoter with a basic nitrogen-containing compound with or without diluent. The diluent is used, if necessary, to provide a suitable viscosity for easy stirring. Typical diluents are lubricating oil and liquid compounds containing only carbon and hydrogen. If desired, ammonium hydroxide may also be added to the reaction mixture to provide a solution of ammonium molybdate. In this improved molybdenum-containing composition reaction, a basic nitrogen compound (e.g., a succinimide), neutral oil, and water are charged to the reactor. The reactor is agitated and heated at a temperature less than or equal to about 120° C., preferably from about 70° C. to about 90° C. Molybdic oxide is then charged to the reactor and the temperature is maintained at a temperature less than or equal to about 120° C., preferably at about 70° C. to about 90° C., until the molybdenum is sufficiently reacted. The reaction time for this step is typically in the range of from about 2 to about 30 hours and preferably from about 2 to about 10 hours.

Typically excess water is removed from the reaction mixture. Removal methods include but are not limited to vacuum distillation or nitrogen stripping while maintaining the temperature of the reactor at a temperature less than or equal to about 120° C., preferably between about 70° C. to about 90° C. The temperature during the stripping process is held at a temperature less than or equal to about 120° C. to maintain the low color intensity of the molybdenum-containing composition. It is ordinarily carried out under reduced pressure. The pressure may be reduced incrementally to avoid problems with foaming. After the desired pressure is reached, the stripping step is typically carried out for a period of about 0.5 to about 5 hours and preferably from about 0.5 to about 2 hours.

Optionally, the reaction mixture may be further reacted with a sulfur source as defined above, at a suitable pressure and temperature not to exceed 120° C. The sulfurization step is typically carried out for a period of from about 0.5 to about 5 hours and preferably from about 0.5 to about 2 hours. In some cases, removal of the polar promoter from the reaction mixture may be desirable prior to completion of reaction with the sulfur source.

In the reaction mixture, the ratio of molybdenum compound to basic nitrogen compound is not critical; however, as the amount of molybdenum with respect to basic nitrogen increases, the filtration of the product becomes more difficult. Since the molybdenum component probably oligomerizes, it is advantageous to add as much molybdenum as can easily be maintained in the composition. Usually, the reaction mixture will have charged to it from 0.01 to 2.00 atoms of molybdenum per basic nitrogen atom. Preferably from 0.4 to 1.0, and most preferably from 0.4 to 0.7, atoms of molybdenum per atom of basic nitrogen is added to the reaction mixture.

The sulfur source is usually charged to the reaction mixture in such a ratio to provide up to 1 atom of sulfur per atom of molybdenum. A preferred ratio is 0.1 atom of sulfur per atom of molybdenum.

The polar promoter, which is preferably water, is ordinarily present in the ratio of 0.5 to 25 moles of promoter per mole of molybdenum. Preferably from 1.0 to 4 moles of the promoter is present per mole of molybdenum.

The color of the molybdenum-containing composition was measured using a Perkin-Elmer Lambda 18 UV-Visible Double-Beam Spectrophotometer. In this test, the visible spectra of molybdenum compositions are recorded at a constant concentration in an isooctane solvent. The spectra represent the absorbance intensity plotted versus the wavelength in nanometers. The spectra extend from the visible region into the near infrared region of the electromagnetic radiation (350 nanometers to 900 nanometers). In this test, the highly colored samples showed increasingly higher absorbance at increasingly higher wavelengths at a constant molybdenum concentration.

The preparation of the sample for color measurement comprises diluting the molybdenum-containing composition with isooctane to achieve a constant molybdenum concentration of 0.00025 g molybdenum per gram of the molybdenum-containing composition/isooctane mixture. Prior to sample measurement the spectrophotometer is referenced by scanning air versus air. The UV visible spectrum from 350 nanometers to 900 nanometers is obtained using a one centimeter pathlength quartz cell versus an air reference. The spectra are offset corrected by setting the 867 nanometer absorbance to zero. Then the absorbance of the sample is determined at 350 nanometers wavelength.

The lubricating oil compositions containing the additives of this invention can be prepared by admixing, by conventional techniques, the appropriate amount of the molybdenum-containing composition with a lubricating oil. The selection of the particular base oil depends on the contemplated application of the lubricant and the presence of other additives. Generally, the amount of the molybdenum containing additive will vary from 0.05 to 15% by weight and preferably from 0.2 to 1% by weight.

The lubricating oil which may be used in this invention includes a wide variety of hydrocarbon oils, such as naphthenic bases, paraffin bases and mixed base oils as well as synthetic oils such as esters and the like. The lubricating oils may be used individually or in combination and generally have viscosity which ranges from 50 to 5,000 SUS and usually from 100 to 15,000 SUS at 38° C.

In many instances, it may be advantageous to form concentrates of the molybdenum containing additive within a carrier liquid. These concentrates provide a convenient method of handling and transporting the additives before their subsequent dilution and use. The concentration of the molybdenum-containing additive within the concentrate may vary from about 0.25 to 90% by weight although it is preferred to maintain a concentration between 1 and 50% by weight.

The final application of the lubricating oil compositions of this invention may be in marine cylinder lubricants as in crosshead diesel engines, crankcase lubricants as in automobiles and railroads, lubricants for heavy machinery such as steel mills and the like, or as greases for bearings and the like. Whether the lubricant is fluid or solid will ordinarily depend on whether a thickening agent is present. Typical thickening agents include polyurea acetates, lithium stearate and the like. The molybdenum containing composition of the invention may also find utility as an anti-oxidant, anti-wear additive in explosive emulsion formulations.

If desired, other additives may be included in the lubricating oil compositions of this invention. These additives include antioxidants or oxidation inhibitors, dispersants, rust inhibitors, anticorrosion agents and so forth. Also, anti-foam agents stabilizers, anti-stain agents, tackiness agents, anti-chatter agents, dropping point improvers, anti-squawk agents, extreme pressure agents, odor control agents and the like may be included.

The lubricant composition of the present invention comprises a major amount of a base oil of lubricating viscosity and a minor amount of the additive formulation described above.

The base oil employed may be any of a wide variety of oils of lubricating viscosity. The base oil of lubricating viscosity used in such compositions may be mineral oils or synthetic oils. A base oil having a viscosity of at least 2.5 cSt at 40° C. and a pour point below 20° C., preferably at or below 0° C. is desirable. The base oils may be derived from synthetic or natural sources. Mineral oils for use as the base oil in this invention include, for example, paraffinic, naphthenic and other oils that are ordinarily used in lubricating oil compositions. Synthetic oils include, for example, both hydrocarbon synthetic oils and synthetic esters and mixtures thereof having the desired viscosity. Hydrocarbon synthetic oils may include, for example, oils prepared from the polymerization of ethylene, i.e., polyalphaolefin or PAO, or from hydrocarbon synthesis procedures using carbon monoxide and hydrogen gases such as in a Fisher-Tropsch process. Useful synthetic hydrocarbon oils include liquid polymers of alpha olefins having the proper viscosity. Especially useful are the hydrogenated liquid oligomers of $C_6$ to $C_{12}$ alpha olefins such as 1-decene trimer. Likewise, alkyl benzenes of proper viscosity, such as didodecyl benzene, can be used. Useful synthetic esters include the esters of monocarboxylic acids and polycarboxylic acids, as well as mono-hydroxy alkanols and polyols. Typical examples are didodecyl adipate, pentaerythritol tetracaproate, di-2-ethylhexyl adipate, dilaurylsebacate, and the like. Complex esters prepared from mixtures of mono and dicarboxylic acids and mono and dihydroxy alkanols can also be used. Blends of mineral oils with synthetic oils are also useful.

Thus, the base oil can be a refined paraffin type base oil, a refined naphthenic base oil, or a synthetic hydrocarbon or non-hydrocarbon oil of lubricating viscosity. The base oil can also be a mixture of mineral and synthetic oils.

The following examples are presented to illustrate specific embodiments of this invention and are not to be construed in any way as limiting the scope of the invention.

EXAMPLES

Example 1

250 grams of a bissuccinimide, prepared from a polyisobutenyl (1000 M.W.) succinic anhydride (PIBSA) and a mixture of polyethylene polyamine oligomers available as E-100 polyethyleneamine from Huntsman Chemical Company at a molar ratio of amine to PIBSA of 0.5 to 1, and 162.5 grams of neutral oil were charged to a glass reactor equipped with a temperature controller, mechanical stirrer, and water cooled condenser. The mixture was heated to a molybdation reaction temperature of 70° C. While at reaction temperature, 26.6 grams of molybdenum oxide and 45.8 grams of water were charged to the reactor. The reactor was then held at a reaction temperature of 70° C. for 28 hours. Upon completion of the molybdation reaction, water was removed by distillation that was carried out at temperature 99° C. and a pressure of 25 millimeters of mercury (absolute) or less for approximately 30 minutes.

The product contained 4.01% by weight of molybdenum and 1.98% by weight of nitrogen.

Example 2

384.4 grams of bissuccinimide as prepared in Example 1 and 249.0 grams of neutral oil were charged to a glass reactor equipped with a temperature controller, mechanical stirrer, and water cooled condenser. The mixture was heated to molybdation reaction temperature 70° C. While at reaction temperature, 40.9 grams of molybdenum oxide and 70.4 grams of water were charged to the reactor. The reactor was then held at reaction temperature 70° C. for 18 hours. Upon completion of the molybdation reaction, water was removed by distillation that was carried out at temperature 99° C. and a pressure of 25 millimeters of mercury (absolute) or less for approximately 30 minutes. At a later time, an 18.7 gram sample of this product was charged to a 250 ml round-bottomed flask. 0.007 grams of sulfur were also charged to the flask. The reaction mixture was then heated to a sulfurization temperature of 80° C. The sulfurization reaction was carried out for 0.5 hours. The product contained 2.03% by weight of nitrogen and 3.83% by weight of molybdenum.

Example 3

299.0 grams of a monosuccinimide, prepared from a polyisobutenyl (1000 M.W.) succinic anhydride (PIBSA) and a mixture of diethylene triamine (DETA) and E-100 polyethyleneamine at a molar ratio of amine to PIBSA of 0.65 to 1, and 232.1 grams of neutral oil were charged to a glass reactor equipped with a temperature controller, mechanical stirrer, and water cooled condenser. The mixture was heated to a molybdation reaction temperature of 70° C. While at reaction temperature, 34.3 grams of molybdenum oxide and 58.9 grams of water were charged to the reactor. The reactor was then held at reaction temperature 70° C. for 21 hours. Upon completion of the molybdation reaction, water was removed by distillation that was carried out at temperature 99° C. and a pressure of 25 millimeters of mercury (absolute) or less for approximately 30 minutes. The product contained 1.92% by weight of nitrogen and 4.08% by weight molybdenum.

Example 4

1353.2 grams of monosuccinimide as prepared in Example 3 and 1057.0 grams of neutral oil were charged to a glass reactor equipped with a temperature controller, mechanical stirrer, and water cooled condenser. The mixture was heated to molybdation reaction temperature 90° C. While at reaction temperature, 155.1 grams of molybdenum oxide and 266.8 grams of water were charged to the reactor. The reactor was then held at reaction temperature 90° C. for 7 hours. Upon completion of the molybdation reaction, water was removed by distillation that was carried out at temperature 99° C. and a pressure of 25 millimeters of mercury (absolute) or less for approximately 30 minutes. The reaction mixture was then adjusted to the sulfurization temperature 80° C. 0.80 grams of sulfur were charged to the reactor. The sulfurization reaction was carried out for 0.5 hours. 2585 grams of product were produced comprising 1.97% by weight nitrogen and 4.05% by weight molybdenum.

Example 5

26,659.0 grams of monosuccinimide as prepared in Example 3 and 20,827.0 grams of neutral oil were charged to a glass reactor equipped with a temperature controller, mechanical stirrer, and water cooled condenser. The mixture was heated to molybdation reaction temperature 90° C. While at reaction temperature, 3056.0 grams of molybdenum oxide and 5256.0 grams of water were charged to the reactor. The reactor was then held at reaction temperature 90° C. for 7 hours. Upon completion of the molybdation reaction, water was removed by distillation that was carried out at temperature 99° C. and a pressure of 25 millimeters of mercury (absolute) or less for approximately 30 minutes. The reaction mixture was then adjusted to the sulfurization temperature 80° C. 15.8 grams of sulfur were charged to the reactor. The sulfurization reaction was carried out for 0.5 hours. The product contained 1.90% by weight nitrogen, 4.05% by weight molybdenum and 0.26% by sulfur.

Example 6

321.4 grams of monosuccinimide as prepared in Example 3 and 51.0 grams of neutral oil were charged to a glass reactor equipped with a temperature controller, mechanical stirrer, and water cooled condenser. The mixture was heated to molybdation reaction temperature 90° C. While at reaction temperature, 24.0 grams of molybdenum oxide and 41.2 grams of water were charged to the reactor. The reactor was then held at reaction temperature 90° C. for 7 hours. Upon completion of the molybdation reaction, water was removed by distillation that was carried out at temperature 99° C. and a pressure of 25 millimeters of mercury (absolute) or less for approximately 30 minutes. The reaction mixture was then adjusted to the sulfurization temperature 90° C. 0.17 grams of sulfur were charged to the reactor. The sulfurization reaction was carried out for 0.5 hours. The product contained 3.15% by weight nitrogen, 4.06% by weight molybdenum, and 0.21% by weight sulfur.

Example 7

426.9 grams of monosuccinimide as prepared in Example 3 and 333.2 grams of neutral oil were charged to a glass reactor equipped with a temperature controller, mechanical stirrer, and water cooled condenser. The mixture was heated to molybdation reaction temperature 80° C. While at reaction temperature, 49.0 grams of molybdenum oxide and 42.1 grams of water were charged to the reactor. The reactor was then held at reaction temperature 80° C. for 4 hours. Upon completion of the molybdation reaction, water was removed by distillation that was carried out at temperature 99° C. and a pressure of 25 millimeters of mercury (absolute) or less for approximately 30 minutes. The product contained 2.00% by weight nitrogen and 4.03% by weight molybdenum.

Example 8

399.6 grams of monosuccinimide as prepared in Example 3 and 311.9 grams of neutral oil were charged to a glass reactor equipped with a temperature controller, mechanical stirrer, and water cooled condenser. The mixture was heated to molybdation reaction temperature 80° C. While at reaction temperature, 45.8 grams of molybdenum oxide and 19.7 grams of water were charged to the reactor. The reactor was then held at reaction temperature 80° C. for 4 hours. Upon completion of the molybdation reaction, water was removed by distillation that was carried out at temperature 99° C. and a pressure of 25 millimeters of mercury (absolute) or less for approximately 30 minutes. The product contained 4.04% by weight molybdenum.

Example 9

407.1 grams of monosuccinimide as prepared in Example 3 and 317.8 grams of neutral oil were charged to a glass reactor equipped with a temperature controller, mechanical stirrer, and water cooled condenser. The mixture was heated to molybdation reaction temperature 80° C. While at reaction temperature, 78.1 grams of molybdenum oxide and 67.1 grams of water were charged to the reactor. The reactor was then held at reaction temperature 80° C. for 8 hours. Upon completion of the molybdation reaction, water was removed by distillation that was carried out at temperature 99° C. and a pressure of 25 millimeters of mercury (absolute) or less for approximately 30 minutes. The product contained 1.84% by weight nitrogen and 6.45% by weight molybdenum.

Example 10

390.0 grams of monosuccinimide as prepared in Example 3 and 304.4 grams of neutral oil were charged to a glass reactor equipped with a temperature controller, mechanical stirrer, and water cooled condenser. The mixture was heated to molybdation reaction temperature 80° C. While at reaction temperature, 88.2 grams of molybdenum oxide and 75.8 grams of water were charged to the reactor. The reactor was then held at reaction temperature 80° C. for 22 hours. Upon completion of the molybdation reaction, water was removed by distillation that was carried out at temperature 99° C. and a pressure of 25 millimeters of mercury (absolute) or less for approximately 30 minutes. The product contained 1.80% by weight nitrogen and 7.55% weight molybdenum.

Example 11

10,864.0 grams of monosuccinimide as prepared in Example 3 and 5292.0 grams of neutral oil were charged to a stainless steel reactor equipped with a temperature controller, mechanical stirrer, and water cooled condenser. The mixture was heated to molybdation reaction temperature 80° C. While at reaction temperature, 1602.0 grams of molybdenum oxide and 689.0 grams of water were charged to the reactor. The reactor was then held at reaction temperature 80° C. for 7.8 hours. Upon completion of the molybdation reaction, water was removed by distillation that was carried out at temperature 99° C. and a pressure of 25 millimeters of mercury (absolute) or less for approximately 30 minutes. The reaction mixture was then adjusted to the sulfurization temperature 80° C. 5.3 grams of sulfur were charged to the reactor. The sulfurization reaction was carried out for 0.5 hours. The product contained 1.59% by weight nitrogen, 5.73% by weight molybdenum, and 0.29% by weight sulfur.

Example 12

This example illustrates a molybdation reaction wherein the basic nitrogen reactant is a carboxylic acid amide.

A mixture of 201 grams of a carboxylic acid amide made from isostearic acid and tetraethylene pentamine, 12.9 grams of molybdic oxide, and 22.4 grams of water in toluene was heated at reflux (about 91 to 101° C.) for 1.5 hours. The flask was fitted with a Dean-Stark trap and a total of 16 grams of water was recovered in 0.5 hours. After filtration using diatomaceous earth filter aid, the solvent was stripped under vacuum (50 mmHg absolute) below 100° C., and 131 grams of a green product was isolated. On standing at ambient conditions, the product solidified into a waxy material. Analysis showed a molybdenum content of 3.3% by weight, and color intensity of 1.5 D using ASTM 1500 and 1.3 D using ASTM D6045.

Example 13

417.9 grams of monosuccinimide as prepared in Example 3 and 326.2 grams of neutral oil were charged to a glass reactor equipped with a temperature controller, mechanical stirrer, and water cooled condenser. The mixture was heated to molybdation reaction temperature 80° C. While at reaction temperature, 47.9 grams of molybdenum oxide and 82.4 grams of water were charged to the reactor. The reactor was then held at reaction temperature 80° C. for 4.0 hours. Upon completion of the molybdation reaction, water was removed by distillation that was carried out at temperature 99° C. and a pressure of 25 millimeters of mercury (absolute) or less for approximately 30 minutes. 798 grams of product were produced comprising 2.01% by weight nitrogen and 4.00% by weight molybdenum.

Example 14

272.8 grams of monosuccinimide as prepared in Example 3 and 260.5 grams of neutral oil were charged to a glass reactor equipped with a temperature controller, mechanical stirrer, and water cooled condenser. The mixture was heated to molybdation reaction temperature 80° C. While at reaction temperature, 49.1 grams of molybdenum oxide and zero grams of water were charged to the reactor. The reactor was then held at reaction temperature 80° C. for 7.25 hours. A large amount of molybdenum oxide was unreacted.

Example 15

9060.0 grams of monosuccinimide as prepared in Example 3 and 7071.0 grams of neutral oil were charged to a stainless steel reactor equipped with a temperature controller, mechanical stirrer, and water cooled condenser. The mixture was heated to molybdation reaction temperature 80° C. While at reaction temperature, 1737.0 grams of molybdenum oxide and 747.0 grams of water were charged to the reactor. The reactor was then held at reaction temperature 80° C. for 7.4 hours. Upon completion of the molybdation reaction, water was removed by distillation that was carried out at temperature 99° C. and a pressure of 25 millimeters of mercury (absolute) or less for approximately 1 hour. The reaction mixture was then adjusted to the sulfurization temperature 84° C. 5.6 grams of sulfur were charged to the reactor. The sulfurization reaction was carried out for 0.5 hours. Product was produced comprising 6.4% by weight molybdenum and 0.29% by weight sulfur.

Example 16

1043.7 grams of monosuccinimide as prepared in Example 3 and 810.0 grams of neutral oil were charged to a glass reactor equipped with a temperature controller, mechanical stirrer, and water cooled condenser. The mixture was heated to molybdation reaction temperature 75° C. While at reaction temperature, 119.7 grams of molybdenum oxide and 206.0 grams of water were charged to the reactor. The reactor was then held at reaction temperature 90° C. for 7.0 hours. Upon completion of the molybdation reaction, water was removed by distillation that was carried out at temperature 99° C. and a pressure of 20 millimeters of mercury (absolute) or less for approximately 1 hour. Product was filtered through a Celite pressure filter. Product was produced comprising 4.07% by weight molybdenum and had a color 5.0 D.

Example 17

9060.0 grams of monosuccinimide as prepared in Example 3 and 7071.0 grams of neutral oil were charged to a stainless steel reactor equipped with a temperature controller, mechanical stirrer, and water cooled condenser. The mixture was heated to molybdation reaction temperature 80° C. While at reaction temperature, 1737.0 grams of molybdenum oxide and 747.0 grams of water were charged to the reactor. The reactor was then held at reaction temperature 80° C. for 6.25 hours. Upon completion of the molybdation reaction, water was removed by distillation that was carried out at temperature under 120° C. and a reduced pressure for approximately 1 hour.

Table 1 provides the color intensity for the molybdenum-containing compositions of the present invention.

TABLE 1

Color Intensity Results

| Example | Absorbance units at 350 nanometers |
|---------|-----------------------------------|
| 1  | 0.495 |
| 2  | 0.644 |
| 3  | 0.315 |
| 5  | 0.416 |
| 7  | 0.303 |
| 8  | 0.299 |
| 9  | 0.247 |
| 10 | 0.203 |
| 11 | 0.242 |

As illustrated in Table 1, the absorbance of the molybdenum-containing compositions of the invention is less than 0.7 absorbance units at 350 nanometers. These results indicate that maintaining the process temperature at or below 120° C. causes a low color intensity.

Comparative Examples

The following examples illustrate the process of making a molybdenum containing composition carried out at a temperature greater than 120° C. during the molybdation reaction, stripping and/or sulfurization steps. This procedure follows the process according to King, U.S. Pat. No. 4,263,152.

To a 1-L, three-necked, round-bottomed glass flask, fitted with a mechanical stirrer, a heating mantle, temperature probe for controlling and measuring the temperature, and water-cooled condenser, were charged 269.3 grams of mono-succinimide dispersant (950 MW, 2.07% N), 25.2 grams of molybdic oxide, 43 grams of water, and 135 grams of Chevron 350H thinner, which is a hydrocarbon thinner.

Comparative Example A

The reaction mixture was heated while stirring at reflux (about 100° C.) for 2 hours. The flask was fitted with a Dean-Stark trap and the reaction mixture was heated to 170° C. for 2 hours, recovering about 40 grams of water. The product was filtered over Celite at about 150° C., and half the filtrate was stripped at 170° C. under house vacuum to remove the solvent for about 1.5 hours. Analysis showed a molybdenum content of 6.0% by weight, a sulfur content of 0.7% which is attributed to sulfur in the base oil, and a color of 3.0 DDD using ASTM D1500. This product had an absorbance intensity of greater than 1.5 at a wavelength of 350 nanometers.

Comparative Example B

To the second half of the filtrate of Comparative Example A was added elemental sulfur, sufficient to give a Charge Mole Ratio (CMR) (S/Mo) of ½. After reacting at 170° C. for 4 hours, the solvent was stripped at 170° C. under house vacuum for 1 hour. Analysis gave a molybdenum content of 6.0% by weight, a sulfur content of 2.6% by weight, nitrogen content of 1.9% by weight, and a color of 4.5 DDD using ASTM D1500. Moreover, this product had an absorbance intensity of greater than 1.5 at a wavelength of 350 nanometers.

Comparative Example C

For comparison, a product from a commercial production (CMR (S/Mo)=2/1) gave a molybdenum content of 6.1% by weight, sulfur content of 3.7% by weight, and a color of 5.5 DDD using ASTM D1500. This product had an absorbance intensity of greater than 1.5 at a wavelength of 350 nanometers.

Performance Results

Oxidation Bench Test

The molybdenum-containing composition of the present invention was added to a lubricating oil and the effect of oxidation was analyzed. An oxidation bench test was performed on the molybdenum-containing composition of King et al., U.S. Pat. No. 4,263,152, and the molybdenum-containing composition of the present invention. These test results were compared and the results of the test indicate that the light colored molybdenum-containing composition of the present invention is an effective anti-oxidant.

Oxidation studies of the products of selected examples were carried out in a bulk oil oxidation bench test as described by E. S. Yamaguchi et al. in *Tribology Transactions*, Vol. 42 (4), 895-901 (1999). In this test, the additive to be tested was added to a formulated base oil containing 6% succinimide dispersant, (25 mM/kg) overbased calcium sulfonate, (25 mM/kg) calcium phenate, (13 mM/kg) ZnDTP, and 5 ppm foam inhibitor in a Group II base oil. In this test, the rate of oxygen uptake at constant pressure by a given weight of oil at 170° C. was monitored. The time required to take-up 250 mL $O_2$ per 25 grams sample was designated as induction time; however, results are reported for convenience as time required to take-up 1 L $O_2$ per 100-gram sample. In this test, the longer induction time corresponds to more effective antioxidant. Bench test results are generally reproducible to within ±0.5 hours.

for the combined additives. Similarly for the molybdenum-containing composition for Comparative Example C, the calculated induction time did not increase, but the anti-oxidant effect for the combined additives was enhanced by 25%. With an enhanced anti-oxidant effect, less of the molybdenum-containing composition can be used while obtaining the same anti-oxidant benefits.

In the present invention, the actual induction time for the molybdenum-containing composition as in Example 16 is 8.3 hours. In the presence of Irganox L-57 the actual induction

TABLE 2

Oxidation Bench Test Results of Molybdenum-Containing Compositions

| Example No. | Irganox L-57 Additive in Test Oil Wt % | Sulfurization Reaction Temperature ° C. | Sulfurization Reaction Time Hours | S Conc. in Test Oil ppm | Mo Conc. in Test Oil[1] Ppm | Actual Induction time, hr | Calcd Induction time, hr | % anti-oxidant enhancement |
|---|---|---|---|---|---|---|---|---|
| Reference Oil | 0 | — | — | — | 0 | 6.7 | — | — |
| Reference Oil | 0.10 | — | — | — | 0 | 14.0 | — | — |
| Comparative Example A | 0 | 170 | 2 | 0 | 320 | 8.3 | — | — |
| Comparative Example C | 0 | 170 | 2 | 214 | 320 | 8.3 | — | — |
| Comparative Example A | 0.10 | 170 | 2 | 0 | 320 | 17.3 | 15.6 | 10.9 |
| Comparative Example C | 0.10 | 170 | 2 | 214 | 320 | 19.5 | 15.6 | 25.0 |
| Reference Oil | 0 | — | — | — | 0 | 7.2 | — | — |
| Reference Oil | 0 | — | — | — | 0 | 6.5 | — | — |
| Reference Oil | 0.13 | — | — | — | 0 | 15.6 | — | — |
| Example 15 | 0 | 80 | 0.5 | 2.1 | 320 | 8.3 | — | — |
| Example 15 | 0 | 80 | 0.5 | 2.1 | 320 | 7.8 | — | — |
| Example 15 | 0 | 80 | 0.5 | 3.0 | 450 | 9.3 | — | — |
| Example 15 | 0 | 80 | 0.5 | 4.2 | 640 | 9.5 | — | — |
| Example 15 | 0.10 | 80 | 0.5 | | 320 | 21.3 | 15.1 | 41.0 |
| Example 15 | 0.13 | 80 | 0.5 | | 320 | 22.6 | 16.7 | 35.3 |
| Example 16 | 0 | 80 | 0 | 0 | 320 | 5.6 | — | — |
| Example 16 | 0 | 80 | 0 | 0 | 320 | 6.2 | — | — |
| Example 16 | 0 | 80 | 0 | 0 | 447 | 6.1 | — | — |
| Example 16 | 0 | 80 | 0 | 0 | 447 | 6.9 | — | — |
| Example 16 | 0 | 80 | 0 | 0 | 447 | 7.0 | — | — |
| Example 17 | 0 | 80 | 0 | 0 | 320 | 7.8 | — | — |

[1]Test Oil Formulation (Reference Oil): molybdenum compound in ppm Mo; 6% succinimide, (25 mM/kg) overbased calcium sulfonate, (25 mM/kg) calcium phenate, (13 mM/kg) ZnDTP, 5 ppm foam inhibitor in Chevron 240N/500N base oil (50/50).

A molybdenum-containing composition was prepared according to the method in King et al., U.S. Pat. No. 4,263,152. A required amount of the molybdenum-containing composition is top-treated into the test oil formulation (i.e., reference oil); and the actual induction time (hours to take-up 1 L $O_2$ per 100 g sample) increases with the addition of the molybdenum containing compound. For example, as indicated in Table 2, the hours to 1 L $O_2$ uptake (actual induction time) for the reference material is measured at 6.7 hours. The induction time for Comparative Example A, prepared according to the procedure of King et al., U.S. Pat. No. 4,263,152, without the addition of Irganox L-57 diphenylamine at 170° C. is 8.3 hours. This result indicates that the molybdenum-containing composition acts as an antioxidant (e.g. the actual induction time is higher than that of the reference material by 1.6 hours). The actual induction time for Comparative Example A with Irganox L-57 at 170° C. is 17.3 hours. The calculated induction time for the presence of two inhibitors (i.e., a molybdenum-containing composition and Irganox L-57) is 15.6 hours. The experimentally obtained value is higher than the calculated value (i.e. calculated value=induction time for molybdenum-containing composition plus induction time for Irganox L-57 minus induction time of reference) and shows an enhanced anti-oxidant effect time increased to 21.3 hours. The calculated induction time for the presence of two inhibitors (i.e., molybdenum-containing composition and Irganox L-57) is 15.1 hours. The experimentally obtained value is higher than the calculated value (calculated value equals actual induction time for molybdenum-containing composition plus induction time for Irganox L-57 minus induction time of reference) showing an enhanced anti-oxidant effect of 41%. This result shows that the molybdenum-containing composition of the present invention is a more effective anti-oxidant than the molybdenum-containing composition of King et al., U.S. Pat. No. 4,263,152.

What is claimed is:

1. A product prepared by a process comprising: (a) reacting an acidic molybdenum compound or salt thereof and a basic nitrogen compound selected from the group consisting of succinimides, carboxylic acid amides, hydrocarbyl monoamines, hydrocarbon polyamines, Mannich bases, phosphonoamides, thiophosphonamides, phosphoramides, dispersant viscosity index improvers, and mixtures thereof, to form a molybdenum complex wherein the temperature of the reaction is maintained at or below about 120° C.; and (b) sulfurizing the resulting product of step (a) at a temperature at or below 120° C. and wherein the sulfur to molybdenum atomic ratio is less than 0.1:1 for a period of time sufficient to provide an oil-soluble molybdenum containing composition having an absorbance intensity of less than 0.7 at a wavelength of 350 nanometers as measured in a one centimeter path-length quartz cell in a UV-Visible spectrophotometer by diluting the molybdenum containing composition with isooctane to a constant molybdenum concentration of 0.00025 grams of molybdenum per gram of the diluted molybdenum containing composition.

2. A product prepared by a process comprising: (a) reacting an acidic molybdenum compound or salt thereof and a basic nitrogen compound selected from the group consisting of succinimides, carboxylic acid amides, hydrocarbyl monoamines, hydrocarbon polyamines, Mannich bases, phosphonoamides, thiophosphonamides, phosphoramides, dispersant viscosity index improvers, and mixtures thereof, to form a molybdenum complex wherein the temperature of the reaction is maintained at or below about 120° C.; (b) stripping the product of (a) at a temperature at or below about 120° C.; and (c) sulfurizing the resulting product at a temperature at or below 120° C. and wherein the sulfur to molybdenum atomic ratio is about 0.1:1 or less for a period of time sufficient to provide an oil-soluble molybdenum containing composition having an absorbance intensity of less than 0.7 at a wavelength of 350 nanometers as measured in a one centimeter path-length quartz cell in a UV-Visible spectrophotometer by diluting the molybdenum containing composition with isooctane to a constant molybdenum concentration of 0.00025 grams of molybdenum per gram of the diluted molybdenum containing composition.

3. A lubricating oil composition comprising an oil of lubricating viscosity and from 0.05 to 15% by weight of the product of claim 1.

4. A lubricating oil composition comprising an oil of lubricating viscosity and from 0.05 to 15% by weight of the product of claim 2.

5. A lubricating oil concentrate composition comprising an oil of lubricating viscosity and from 15 to 90% weight of the product of claim 1.

6. A lubricating oil concentrate composition comprising an oil of lubricating viscosity and from 15 to 90% by weight of the product of claim 2.

7. The lubricating oil composition of claim 3, further comprising an additive selected from the group consisting of an antioxidant, dispersant, rust inhibitor, anticorrosion agent, anti-foam agent, stabilizer, anti-stain agent, tackiness agent, anti-chatter agent, dropping point improver, anti-squawk agent, extreme pressure agent, odor control agent and mixtures thereof.

8. The lubricating oil composition of claim 4, further comprising an additive selected from the group consisting of an antioxidant, dispersant, rust inhibitor, anticorrosion agent, anti-foam agent, stabilizer, anti-stain agent, tackiness agent, anti-chatter agent, dropping point improver, anti-squawk agent, extreme pressure agent, odor control agent and mixtures thereof.

* * * * *